US 9,089,126 B2

(12) United States Patent
Faulkner et al.

(10) Patent No.: US 9,089,126 B2
(45) Date of Patent: *Jul. 28, 2015

(54) METHODS AND APPARATUS FOR ORGAN SUPPORT

(71) Applicants: Donald G. Faulkner, Charlotte, NC (US); John L. Robertson, Floyd, VA (US)

(72) Inventors: Donald G. Faulkner, Charlotte, NC (US); John L. Robertson, Floyd, VA (US)

(73) Assignee: BioMedInnovations, LLC, Denver, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/711,395

(22) Filed: Dec. 11, 2012

(65) Prior Publication Data

US 2013/0102059 A1  Apr. 25, 2013

Related U.S. Application Data

(63) Continuation of application No. 12/184,701, filed on Aug. 1, 2008, now Pat. No. 8,329,450.

(51) Int. Cl.
*A01N 1/00* (2006.01)
*A01N 1/02* (2006.01)
*A61M 1/36* (2006.01)
*A61M 1/10* (2006.01)
*A61N 1/36* (2006.01)

(52) U.S. Cl.
CPC ........... *A01N 1/0247* (2013.01); *A61M 1/1005* (2014.02); *A61M 1/3613* (2014.02); *A61M 1/3639* (2013.01); *A61N 1/3605* (2013.01); *A61M 2205/3553* (2013.01); *A61N 1/36007* (2013.01)

(58) Field of Classification Search
CPC ......... A01N 1/0247; A01N 1/00; A01N 1/02; A01N 1/021; A01N 1/0242
USPC ............................... 435/1.1, 1.2, 284.1, 283.1
See application file for complete search history.

(56) References Cited

U.S. PATENT DOCUMENTS

| | | | |
|---|---|---|---|
| 3,639,084 A * | 2/1972 | Goldhaber | 417/394 |
| 4,662,355 A | 5/1987 | Pieronne et al. | |
| 5,051,352 A * | 9/1991 | Martindale et al. | 435/1.2 |
| 6,110,139 A | 8/2000 | Loubser | |
| 2003/0199806 A1* | 10/2003 | Kieval | 604/8 |
| 2006/0210959 A1* | 9/2006 | Dancu et al. | 435/1.2 |

OTHER PUBLICATIONS

Seung Hoon Hyun, International Search Report for PCT/US2009/052447, Feb. 27, 2010, Korean IP Office, Korea.
Athina Nickitas-Etienne, International Preliminary Report on Patentability, Feb. 10, 2011, WIPO, Geneva, Switzerland.

* cited by examiner

*Primary Examiner* — Nathan Bowers
(74) *Attorney, Agent, or Firm* — Trego, Hines & Ladenheim, PLLC

(57) ABSTRACT

An organ support apparatus includes: (a) a fluid circuit defining upstream and downstream legs adapted to be connected to an organ to be supported; (b) a circulation pump connected to the fluid circuit for circulating a process fluid through the fluid circuit and the organ; and (c) a first waveform generator connected to the fluid circuit for impressing a preselected pressure waveform on the process fluid.

4 Claims, 8 Drawing Sheets

US 9,089,126 B2

METHODS AND APPARATUS FOR ORGAN SUPPORT

BACKGROUND OF THE INVENTION

This invention relates generally to organ support and bypass processes, and more particularly to methods and apparatus for carrying out perfusion in a controlled manner.

Numerous medical procedures require extraction of a patient's blood, treatment of the blood by processes such as filtering, oxygenation, and the like, and return of the blood to the patient's body. Examples of such procedures include open heart surgery, organ transplants, membrane oxygenation, and hemodialysis. This type of blood processing is referred to herein as a "bypass" or "body support" process, and typically uses pumps with essentially constant pressure output to circulate the patient's blood through the treatment equipment. Unfortunately, this kind of flow is much different from the flow provided by a patient's heart. It has been found that this constant-pressure flow can have undesirable side effects including brain disorders, blood clot formation, and limited or reduced circulation, especially in flow restrictive areas. This places undesirable limits on the usage of this type of equipment.

It is also known that some devices use a similar process to circulate an aqueous organ preservation fluid, such as "Belzer's solution", through organs which have been harvested for transplantation. This action sustains the organ while it is outside the body by attempting to preserve functioning, and increases the limited "shelf life" of transplant organs compared to conventional chilled storage. However, known organ support processes encounter the same problems as conventional bypass, namely that the flow pressure characteristics of the process fluid are much different than that provided by a patient's heart. Furthermore, flow which is only "pushed" by a pump is subject to the formation of gaseous, fibrinothrombocytic, and fat emboli which are difficult to remove, and which can interfere with flow and cause organ damage.

BRIEF SUMMARY OF THE INVENTION

These and other shortcomings of the prior art are addressed by the present invention, which provides a method for perfusing fluid through organs and tissues. The system and method described herein act as a "cardiovascular emulator" to provide fluid flow in a manner very similar to a heart.

According to one aspect of the invention, an organ support apparatus includes: (a) a fluid circuit defining upstream and downstream legs adapted to be connected to an organ to be supported; (b) a circulation pump connected to the fluid circuit for circulating a process fluid through the fluid circuit and the organ; and (c) a first waveform generator connected to the fluid circuit for impressing a preselected pressure waveform on the process fluid.

According to another aspect of the invention, an organ support apparatus includes: (a) a fluid circuit defining upstream and downstream legs adapted to be connected to an organ to be supported; (b) a circulation pump connected to the fluid circuit for circulating a process fluid through the fluid circuit and the organ; (c) a first waveform generator disposed in the upstream leg for impressing a preselected first pressure waveform on the process fluid before it is delivered to the organ; and (d) a second waveform generator connected in the downstream leg of the fluid circuit for impressing a preselected second pressure waveform on the downstream pressure applied to the organ.

According to another aspect of the invention, a method of supporting an organ includes: (a) circulating a process fluid through a fluid circuit comprising an upstream leg, the organ, and a downstream leg; (b) impressing a preselected first waveform profile upon the fluid flow in the upstream leg before it enters the organ; and (c) impressing a preselected second waveform profile upon the fluid flow in the downstream leg.

According to yet another aspect of the invention, a method of supporting an organ includes: (a) circulating a process fluid through a fluid circuit comprising an upstream leg, the organ, and a downstream leg; and (b) independently controlling the pressure applied to the process fluid at both upstream and downstream connections to the organ.

BRIEF DESCRIPTION OF THE DRAWINGS

The invention may be best understood by reference to the following description taken in conjunction with the accompanying drawing figures in which.

DETAILED DESCRIPTION OF THE INVENTION

Figure 1:
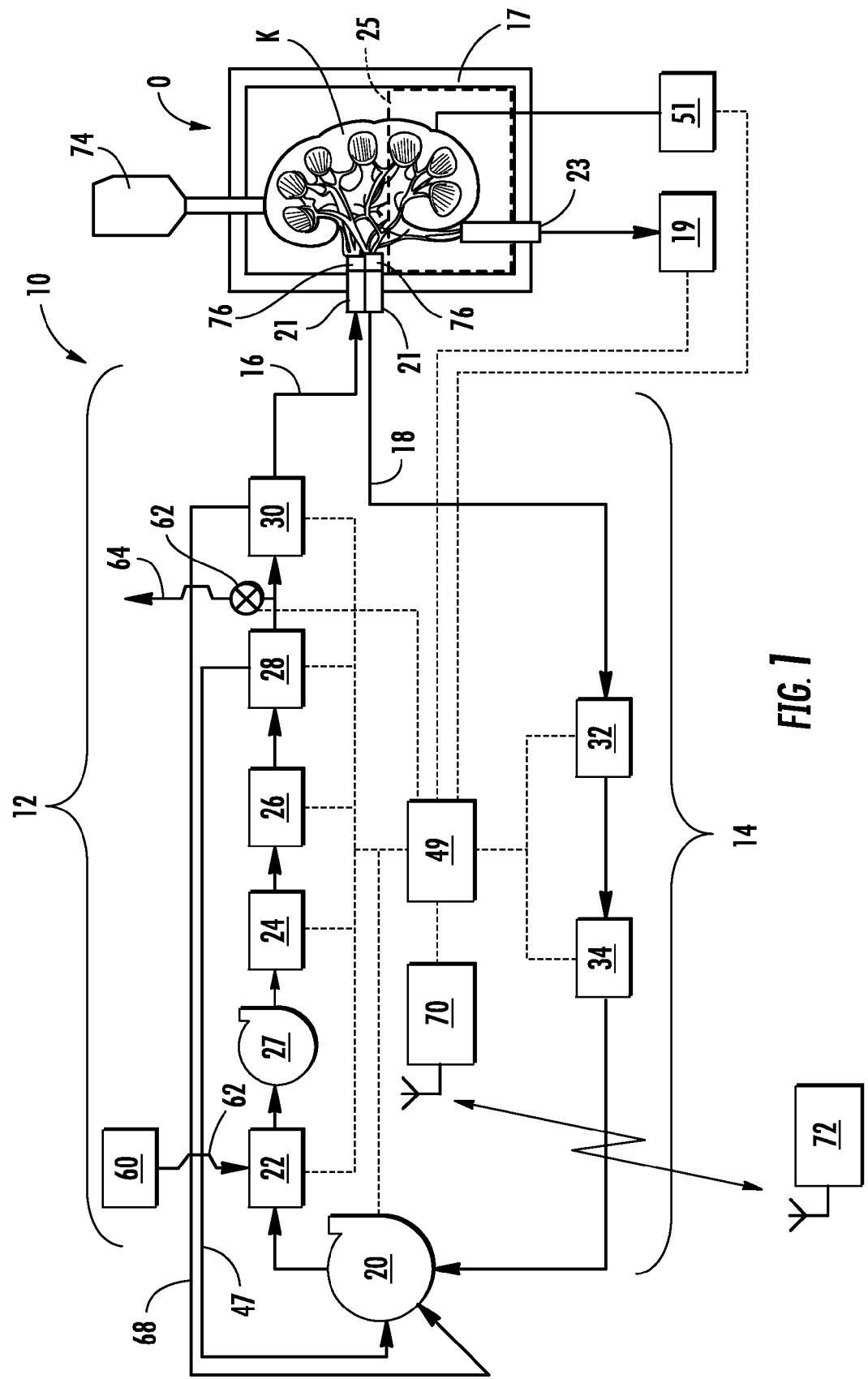
FIG. 1 is a schematic view of a organ support apparatus constructed according to an aspect of the present invention.

Referring to the drawings wherein identical reference numerals denote the same elements throughout the various views, FIG. 1 depicts an organ support apparatus 10 constructed in accordance with the present invention suitable for circulating a fluid through an organ. The apparatus 10 comprises a fluid circuit defined by plastic tubing or another suitable type of conduit, with an upstream leg 12 and a downstream leg 14. The apparatus 10 is connected to an organ or other body process to be supported, depicted generally at "O", by an inlet line 16 and an outlet line 18. The illustrated example is explained in the context of providing support for a kidney "K" which is contained in an enclosure 17 and connected to a waste storage container 19 which receives a urine flow from the kidney K. However, it will be understood that the principles of the present invention are broadly applicable to support of many types of organs both inside and outside the body, as well as different types of body processes. Obviously, the waste storage container 19 would not be needed for other organs. Some of these applications are described in more detail below.

The apparatus 10 comprises, in sequential fluid flow order, a circulation pump 20, a perfusate metering array 22, an oxygenator 24, a heat exchanger 26, a bubble trap 28, a fluid waveform generator 30, the organ O, a sensor array 32, and a biological filter 34 for filtering endogenous or exogenous material from the process fluid (e.g. a hemodialysis filter).

The circulation pump 20 may be any type of pump which can provide the required flow rates and pressures and is hygienic. The process fluid may be blood containing cells, plasma, and expanders, or other therapeutic fluids containing complex molecules. Examples of process fluids that may be used in different processes include aqueous organ preservatives such as "University of Wisconsin solution", "Belzer's solution", whole blood, plasma, serum, crystalloid and non-crystalloid expanders, and oxygen-carrying molecules. The initial process fluid charge volume of the apparatus 10 is envisioned to be in the range of about 500 mL to about 1000 mL. Preferably the circulation pump 20 is a type which does not tend to damage these fluid components. Examples of suitable pumps include peristaltic and centrifugal types. The discharge pressure of the pump 20 may be in the range of about 100 to about 600 mm Hg. Optionally, an auxiliary circulation pump 27 may be provided between the perfusate metering array 22 and the oxygenator 24 and/or between the organ outflow stream and the sensor array 32.

The perfusate metering array 22 comprises a manifold communicating with the fluid circuit and includes inlets for admitting one or more fluid components into the fluid circuit. Optionally, a pumping apparatus for metering one or more fluid components into the fluid circuit, such as make-up process fluid, may be incorporated into the metering array 22. The fluid components may be supplied from an external source such as a tank or reservoir which is depicted schematically at 60, connected to the metering array 22 with a supply line 62.

The oxygenator 24 is of a known type which is configured to introduce oxygen into the fluid stream from an external source, such as bottled gaseous oxygen. The oxygenator 24 may be a separate unit or combined with the heat exchanger 26, which operates to heat or cool the process fluid to a desired temperature.

Figure 2:
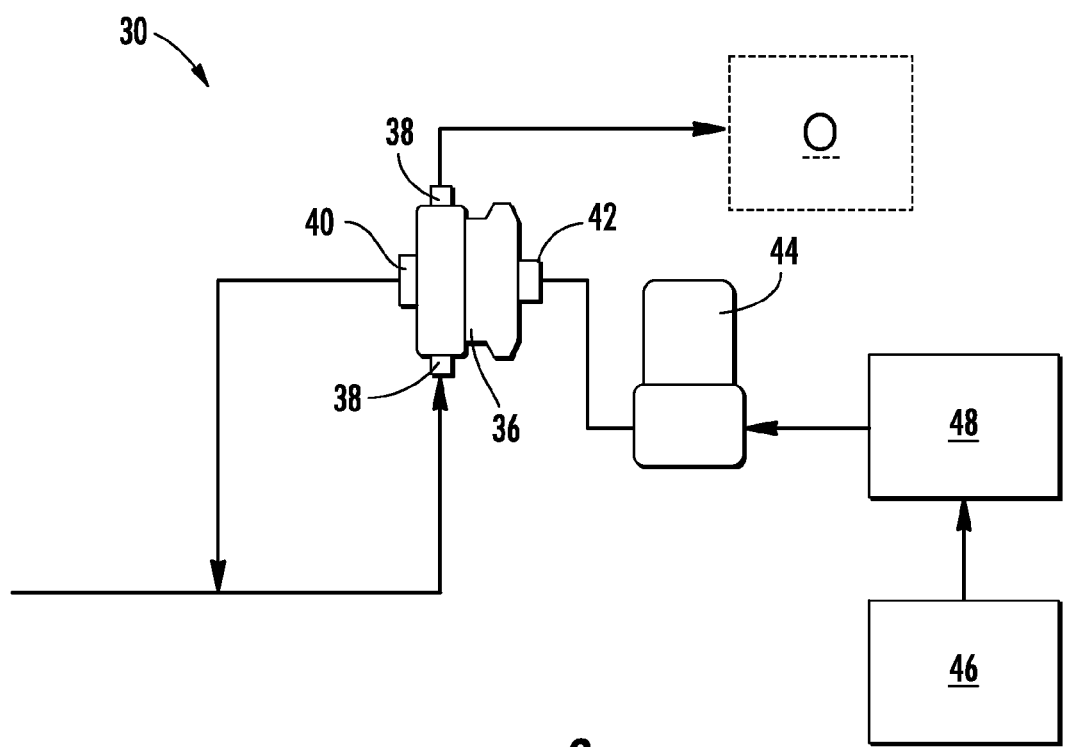
FIG. 2 is a schematic view of a pressure waveform generator of the organ support apparatus of FIG. 1.

The bubble trap 28 is of a conventional type which forces the process fluid past a microporous hydrophobic membrane. Its purpose is to remove any gas bubbles from the process flow that could impede flow in the circulating loop, The waveform generator 30 is effective to receive process fluid from the upstream leg 12 of the fluid circuit and reduce the pressure to a suitable value for the organ O, for example about 40 to about 180 mm Hg and to apply a pressure profile thereto, so that the organ O receives a pulsating flow which mimics the flow characteristics of a patient's heart. In the illustrated example, shown in FIG. 2, the waveform generator 30 comprises a diaphragm-type pressure regulator 36 having a pair of process ports 38 connected to the fluid circuit, a bypass port 40 connected to a point upstream of the waveform generator 30, and a reference port 42 which is connected to an electropneumatic (E/P) transducer 44 of a known type. Suitable waveform generators of this type are available from Insight Process Solutions LLC, Hendersonville, N.C. 28791 USA. The E/P transducer 44 is in turn connected to a programmable electronic controller 46 or computer through an input/output (I/O) card 48.

The apparatus 10 may include a means for preventing over-pressurization of the waveform generator 30. In the illustrated example this is provided by a return line 47 from the output end of the bubble trap 28 to the inlet of the circulation pump 20. This relief flow may be a constant bleed or it may be controlled by a relief valve (not shown) set at a predetermined pressure.

A dump line 64 may be provided, for example downstream of the bubble trap 28, coupled to a drain or a suitable waste container (not shown). Flow from the fluid circuit to the dump line may be controlled by a purge valve 66, which may be remotely controlled.

Referring again to FIG. 1, the waveform generator 30, which is described in detail below, receives blood flow from the pump 14 and applies a cyclic pressure pulse thereto, as commanded by the controller 46, so that the organ O receives a pulsating flow which mimics the flow characteristics of the patient's heart. An exhaust line 68 routes exhaust fluid from the waveform generator 30 back to an upstream portion of the apparatus, for the example the inlet of the circulation pump 20.

Figure 3:
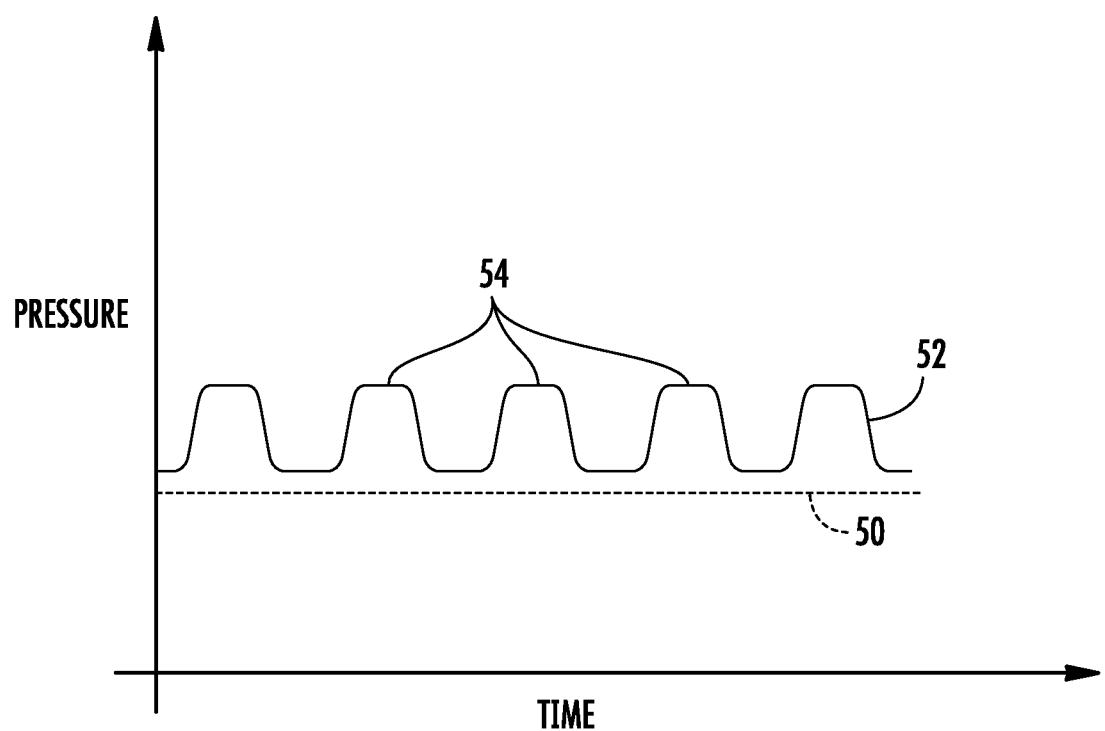
FIG. 3 is a schematic graph of a flow characteristic of the apparatus in operation.

FIG. 3 illustrates an example of the flow characteristics that can be obtained. The dashed line 50 represents the essentially constant pressure output of the circulation pump 20, while the solid line 52 represents the total pressure after the fluid passes through the waveform generator 30. Appropriate feedback signals are provided to the controller 46, representative of the output of the apparatus 10. In the illustrated example, the flow has a pulsating pressure with peaks 54 occurring at regular intervals. A quasi-square-wave flow characteristic is shown; however, by careful control programming, almost any wave shape desired can be obtained. This allows the apparatus 10 to closely emulate the flow characteristics of the patient's heart or to generate specific preferred waveforms as determined by the physician or technician involved in a particular procedure. It is thought that this will maximize the "shelf life" of the organ O being transported, or if used to support the patient directly, will eliminate or reduce undesirable affects, including brain disorders, normally associated with heart-lung bypass and membrane oxygenator equipment.

The organ enclosure 17 (see FIG. 1) provides physical protection to the organ (in this case the kidney K). It may be constructed from sterilizable transparent medical-grade polymer, and is provided with connections 21 between the artery and vein of the kidney K (for example) and the inlet and outlet lines 16 and 18 respectively. Sensors 76 may be provided inside the enclosure 17, operably coupled to the artery or vein and effective to measure pressure, flow, and/or temperature of the fluid flowing in and out of the kidney K. There is also a connection 23 to the ureter, to allow urine to drain to the waste storage container 19. The waste container 19 may be provided with sensors for measuring aspects of the urine such as volume, mass, pH, temperature, flow rate, and quantity of metabolites. In the illustrated example, the enclosure includes a structured gelatin 25 that supports the kidney K while evenly distributing the pressure.

The sensor array 32 includes one or more sensors for evaluating the condition of the of the process fluid in the fluid circuit, such as flow rate, pressure, temperature, oxygenation levels, gas and/or chemical composition, and the like. Known types of transducers and sensors are utilized to generate signals representative of each measured parameter.

A central controller 49 is provided for the apparatus 10. The central controller 49 includes or more processors and may be a general-purpose microcomputer of a known type, such as a PC-based computer, or may be a custom processor, or may incorporate one or more programmable logic controllers (PLC). The central controller 49 is operably connected to the individual functional components of the apparatus 10 in order to receive data and/or transmit commands to each component. For example, the central controller 49 receives data about the process fluid condition from the sensor array 32. It transmits pressure waveform commands to the waveform generator 30 to maintain a desired pressure waveform entering the organ O. The central controller 49 may communicate directly with the functional components of the apparatus 10, or through intermediate devices such as the controller 46 described above. The data connections between the central controller 49 and the individual components may be through wired or wireless channels. The central controller 49 may be used for feedback control of the components in the apparatus 10 based on one or more inputs. For example, the composition of the process fluid may be varied depending on various metabolite levels in the kidney K. Furthermore, pressure, flow, and/or temperature data from the sensors 76 may be used to adjust or "tune" the operating parameters of the apparatus 10.

The apparatus 10 may be provided with a transceiver 70 coupled to the central controller 49. The purpose of the transceiver 70 is to bidirectionally exchange telemetry data with a remote transceiver 72, which may in turn be coupled to a remote controller, computer, or data server (not shown). This may be used to monitor the performance of the apparatus 10 and/or to transmit commands to the apparatus 10 remotely. The data connection between the central controller 49 and the remote transceiver 72 may be wired or wireless.

Optionally, the apparatus 10 may include an electrical stimulator 51 coupled to the central controller 49 and to the organ O via electrodes. The electrical stimulator 51 is essentially a controllable electrical power supply and can be programmed to provide the organ O with a recurrent electrical pulse, for example between about 1.0 and 2.5 millivolts. The charge may be positive or negative polarity, with the ability to switch polarity. The preprogrammed electrical pulse may be timed either in phase or out of phase with the fluid pulses described above. The electrical waveform characteristics of the pulse may be varied to suit a particular organ. Furthermore, an external input, for example an ECG or EKG signal (not shown), may be coupled to the electrical stimulator 51 for aiding in the description of the electrical pulse characteristics and/or pulse timing purposes. The electrical pulse is useful in a known manner for diffusing fluid through the organ O.

Optionally, an imager 74 (visual, UV, IR, etc.) may be used to observe the condition of the organ O through a port in the enclosure 17. One example of a suitable imager is a confocal microscope such as the VIVASCOPE device available from Lucid, Inc., Rochester, N.Y. 14623 USA With appropriate programming, the central controller 49 may be automatically flow regulating for different organ tissue masses, thermal conditions that influence vascular elasticity, variable perfusate flow restrictions at the organ level, and variable fluid characteristics (e.g. viscosity, entrained shear sensitive solids, etc.), while precisely maintaining the process fluid flow between narrowly defined systolic and diastolic pressure set points. This will virtually eliminate the potential for permanent capillary damage due to over pressurization of organ vasculature.

Figure 4:
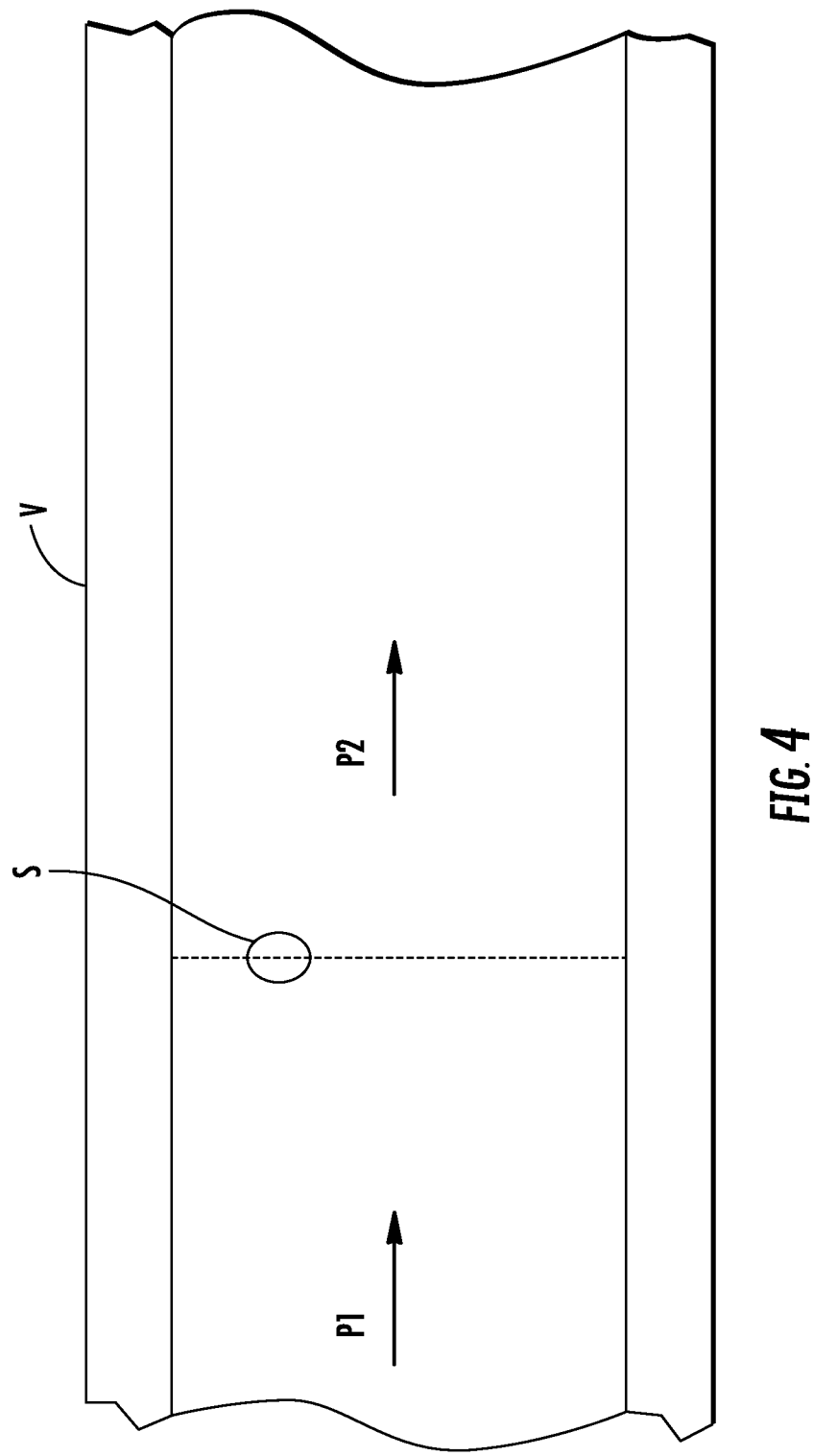
FIG. 4 is a schematic cross-sectional view of a blood vessel containing a solid embolus therein.
Figure 5:
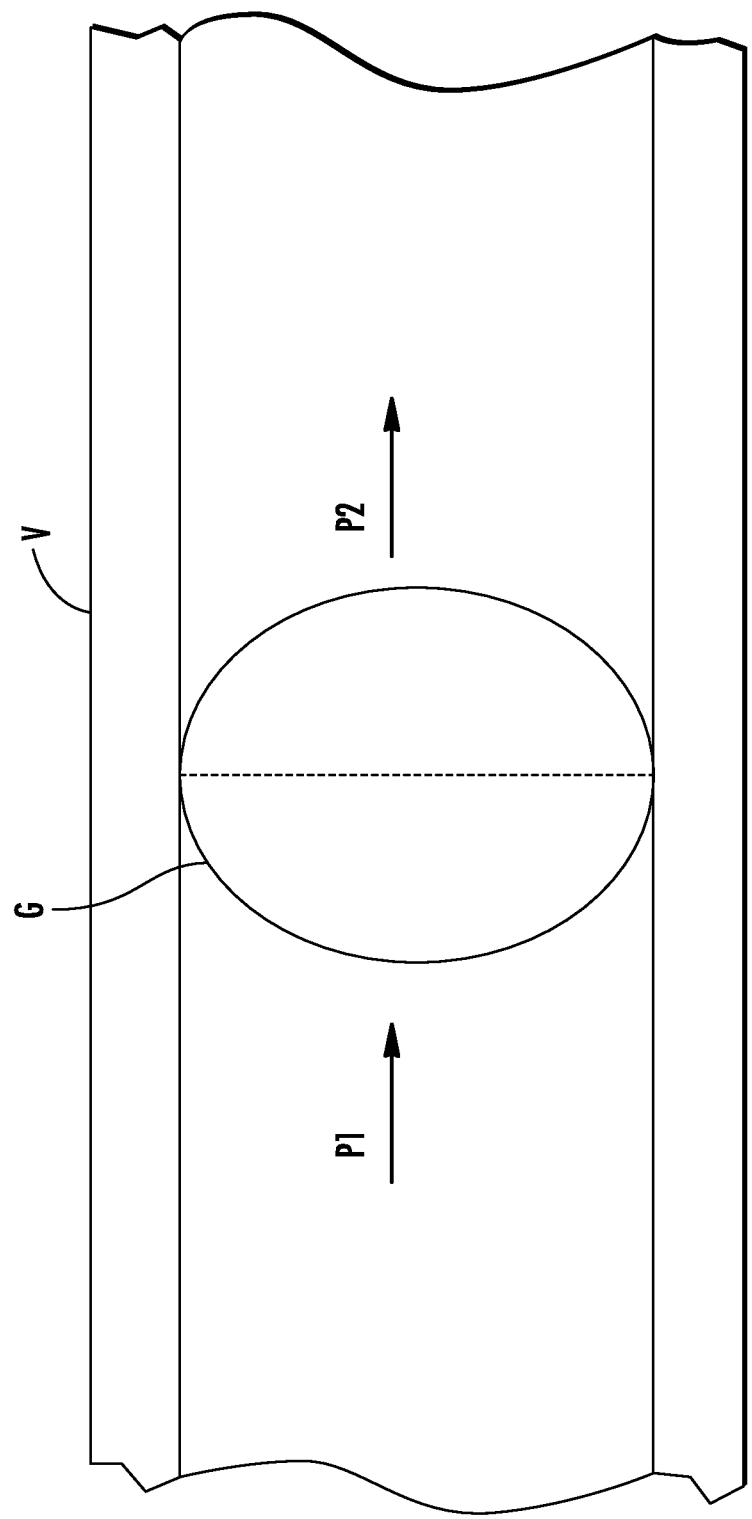
FIG. 5 is a schematic cross-sectional view of a blood vessel containing a gaseous embolus therein.

FIG. 4 illustrates a cross-section of a blood vessel "V" containing a solid embolus "S" therein. Arrows "P1" and "P2" represent the fluid pressure upstream and downstream of the embolus S, respectively. Typically, solid emboli can be forced downstream using constant or pulsating pressure applied from upstream, i.e. by forcing P1 greater than P2. However, as shown in FIG. 5, a gaseous embolus "G" tends to expand within the vessel V, and cannot be effectively moved by increasing or pulsing the upstream pressure P1 alone.

Figure 6:
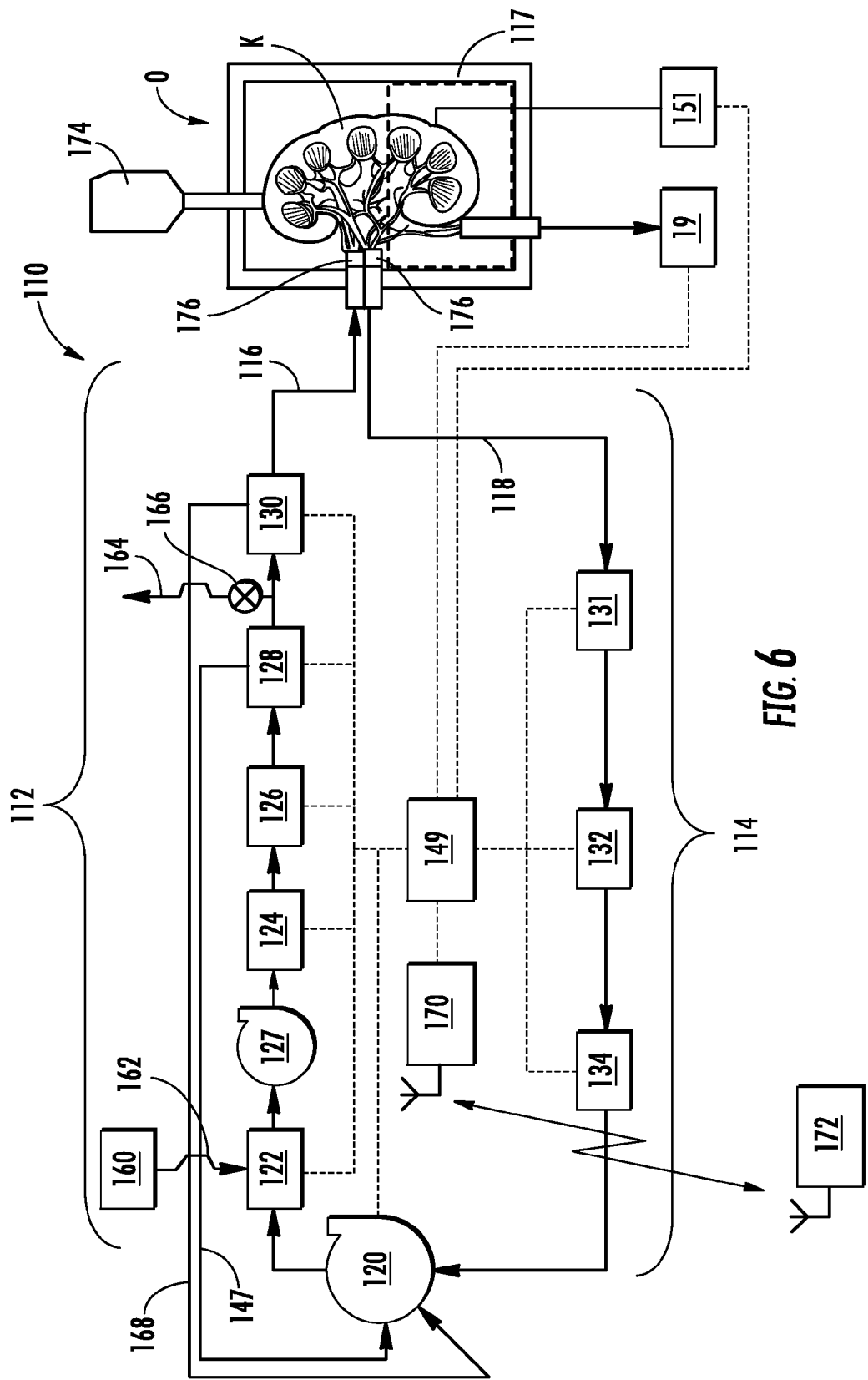
FIG. 6 is a schematic view of an alternative organ support apparatus constructed according to an aspect of the present invention.

Accordingly, FIG. 6 depicts another embodiment of an organ support apparatus 110 which is generally similar to the apparatus described above. It too includes a fluid circuit defined by plastic tubing or another suitable conduit, with an upstream leg 112 and a downstream leg 114. The apparatus 110 is connected to an organ or other body process to be supported, depicted generally at "O", by an inlet line 116 and an outlet line 118. The illustrated example is explained in the context of providing support for a kidney "K" which is contained in an enclosure 117 suitable for storing or transporting the kidney K. Sensors 176 may be provided inside the enclosure 117, operably coupled to the artery or vein and effective to measure pressure, flow, and/or temperature of the fluid flowing in and out of the kidney K.

The apparatus 110 comprises, in sequential fluid flow order, a circulation pump 120, a perfusate metering array 122, supply line and reservoir 162 and 166, optional auxiliary pump 127, an oxygenator 124, a heat exchanger 126, a bubble trap 128, return line 147, purge valve 166 and dump line 164, an upstream fluid waveform generator 130, exhaust line 168, the organ O, a downstream fluid waveform generator 131, a sensor array 132, and a biological filter 134 (e.g. a hemodialysis filter). A central controller 149 is also provided, and the apparatus 110 may include an electrical stimulator 151 similar to the one described above. A transceiver 170, remote transceiver 171, and imager 174 may be provided as well.

Figure 7:
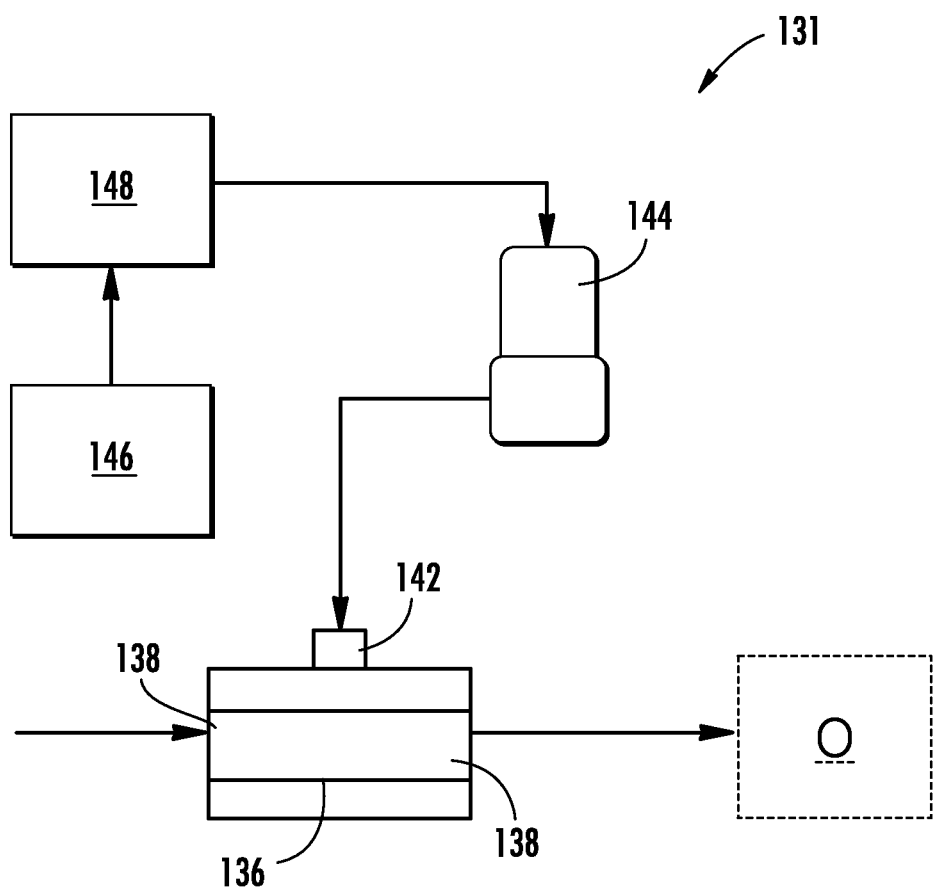
FIG. 7 is a schematic view of a suction waveform generator of the organ support apparatus of FIG. 6.

The downstream waveform generator 131 is shown in FIG. 7. It includes a diaphragm-type device 136 similar in construction to the upstream regulator and includes a pair of process ports 138 connected to the fluid circuit, and a reference port 142 which is connected to an electropneumatic (E/P) transducer 144 of a known type. The E/P transducer 144 is connected to a programmable electronic controller or computer 146 through an input/output (I/O) card 148. The computer 146 may be used to control both the upstream waveform generator 130 and the downstream waveform generator 131.

The downstream waveform generator 131 is effective to precisely regulate the pressure in the fluid circuit downstream of the organ O (i.e. the suction-side pressure), independently from the pressure in the upstream leg 112, regardless of whether the absolute downstream leg pressure is above or below atmospheric pressure. The flow characteristics are similar to those illustrated in FIG. 3, e.g. with suction or pressure peaks occurring at regular intervals. By careful control programming, almost any wave shape desired can be obtained. The waveform applied by the downstream waveform generator 131 may be in or out of phase with the waveform applied by the upstream waveform generator 130, and the pulses may be above or below atmospheric pressure. For example, while the absolute fluid pressure in the entire fluid circuit may be above atmospheric pressure, the pressure in the downstream leg 114 may be substantially lower than that in the upstream leg 112. For example, a kidney K could be supplied with a renal artery input pressure of about 40 to about 180 mm Hg as described above, with the downstream pressure controlled by the downstream waveform generator 131 in the range of about 10 to about 50 mm Hg.

The apparatus 10 or 110 may be used to transition an organ O between various processes in the following manner. When an organ such as a kidney K is harvested from a donor, it will be loaded with the donor's blood and with waste products. When the kidney K is initially connected to the apparatus, a neutral saline solution or other suitable flushing composition may be used as the process fluid and circulated through the apparatus 10 and the kidney K, to flush out the blood and waste products. Using the apparatus 10 provides a much more gentle flushing action than a conventional flush using manual methods.

While the flushing fluid is circulating, the composition of the of the process fluid can be changed at a controlled rate by introducing a desired fluid composition, for example diluted blood containing expanders, nutrients, or other therapeutic fluids as described above, in the supply line 62, while opening the purge valve 66 and exhausting fluid through the dump line 64, to a drain or suitable container. The inlet flow and the purge flow rate may be set at some percentage of the recirculating flow rate through the fluid circuit, such that eventually all of the process fluid will be of the new composition.

In a subsequent step, the process fluid composition can be changed again using the same transition procedure. For example the process fluid might be changed to an organ maintenance, therapeutic, and regenerative chemistry for long-term storage or regeneration of the kidney K. Finally, the process fluid composition may be changed a final time using the transition procedure in order to load the kidney K with a recipient patient's blood type just before implantation.

Figure 8:
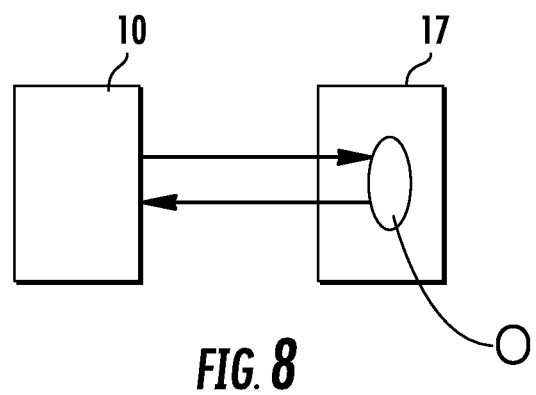
FIG. 8 is a schematic view of an organ support apparatus connected to an organ outside a patient's body.

Regardless of the exact configuration of the organ support apparatus described above, it may be applied in a number of ways. FIG. 8 shows an organ support apparatus 10 connected to an individual organ O in an enclosure 17 located outside the body as described above. In this configuration, the support apparatus 10 would be used to store or to transport the organ O for transplant. This configuration could also be used for nurturing an organ O to regenerate it, and/or growing an organ on a scaffold, by using the metering array 22 to introduce fluids carrying or seeded with therapeutic and regenerative materials, including cells and biologic growth factors, or other fluids having a regenerative effect on the organ O.

Figure 9:
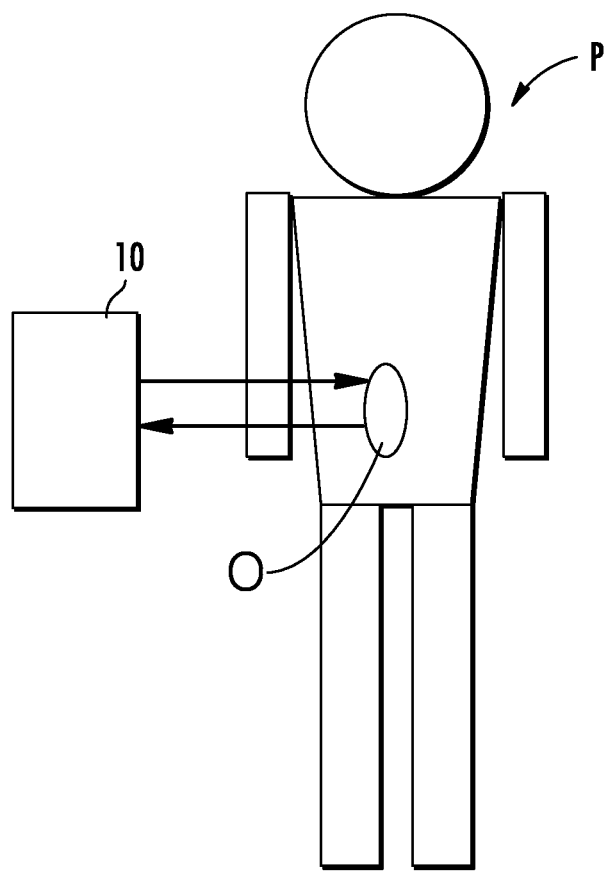
FIG. 9 is a schematic view of an organ support apparatus connected to an organ inside a patient's body.

FIG. 9 shows an organ support apparatus 10 connected to an organ O which is inside a patient "P", i.e. a human or other animal. In this configuration, one or more blood vessels would be disconnected from the patient P and connected to the organ support apparatus 10. This has the effect of isolating the organ O from the rest of the patient's body without requiring removal of the organ or disconnection from vital physiologic structures and tissues, and minimizing organ trauma due to handling procedures and inconsistent blood flow. This configuration is expected to be especially helpful for patients who require aggressive chemotherapies that can cause severe organ damage, such as the treatment of malignancies or metabolic toxicities. In such situations, the organs could be isolated and supported for the duration of chemotherapy, and then reconnected back to the patient's body and placed back "on-line" without having their function impaired and without the need to expose other organs in the patient "P" to the potentially damaging effects of chemotherapy (as an example).

The organ support apparatus and method described above greatly reduces organ tissue related to hypertension (over pressurization) of organ capillaries while effectively perfusing the vascular structure for optimal preservation and long term functionality.

The foregoing has described systems and methods for organ and body process support. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation.

What is claimed is:

1. An organ support apparatus, comprising:
    an enclosure adapted to enclose an organ to be supported and including inlet and outlet connections configured to be coupled to the organ;
    a fluid circuit defining upstream and downstream legs connected to the inlet and outlet connections respectively;
    a circulation pump connected to the fluid circuit for circulating a process fluid through the fluid circuit and the organ;
    a first waveform generator disposed in the upstream leg for impressing a preselected first pressure waveform on the process fluid before it is delivered to the organ, wherein the first waveform generator comprises:
        a first diaphragm-type pressure regulator; and
        a first reference pressure source connected to the pressure regulator; and
    a second waveform generator connected in the downstream leg of the fluid circuit for impressing a preselected second pressure waveform on the downstream pressure applied to the organ, wherein the second waveform generator comprises:
        a second diaphragm-type pressure regulator; and
        a second reference pressure source connected to the second pressure regulator.

2. The organ support apparatus of claim 1 wherein the first reference pressure source comprises:
    a first electropneumatic transducer coupled to the first pressure regulator; and
    an electronic controller coupled to the first electropneumatic transducer and programmed to transmit a signal representative of the preselected waveform to the first electropneumatic transducer.

3. The organ support apparatus of claim 1 wherein the second reference pressure source comprises:
    a second electropneumatic transducer coupled to the second pressure regulator; and
    an electronic controller coupled to the second electropneumatic transducer and programmed to transmit a signal representative of the preselected waveform to the first electropneumatic transducer.

4. The organ support apparatus of claim 1 wherein the fluid circuit includes at least one filter for removing foreign material from the process fluid.

* * * * *